(12) United States Patent
Van Kampen

(10) Patent No.: US 10,265,156 B2
(45) Date of Patent: Apr. 23, 2019

(54) TENDON REPAIR IMPLANT AND METHOD OF IMPLANTATION

(71) Applicant: ROTATION MEDICAL, INC., Plymouth, MN (US)

(72) Inventor: Craig Van Kampen, Oakdale, MN (US)

(73) Assignee: ROTATION MEDICAL, INC, Plymouth, MN (US)

(*) Notice: Subject to any disclaimer, the term of this patent is extended or adjusted under 35 U.S.C. 154(b) by 45 days.

(21) Appl. No.: 15/181,612

(22) Filed: Jun. 14, 2016

(65) Prior Publication Data

US 2016/0361155 A1 Dec. 15, 2016

Related U.S. Application Data

(60) Provisional application No. 62/175,829, filed on Jun. 15, 2015.

(51) Int. Cl.
*A61F 2/08* (2006.01)
*A61F 2/00* (2006.01)

(52) U.S. Cl.
CPC .............. *A61F 2/08* (2013.01); *A61F 2/0063* (2013.01); *A61F 2210/0004* (2013.01); *A61F 2210/0076* (2013.01); *A61F 2250/003* (2013.01); *A61F 2250/0017* (2013.01); *A61F 2250/0018* (2013.01); *A61F 2250/0023* (2013.01)

(58) Field of Classification Search
CPC ......... A61F 2/08; A61F 2/0811; A61F 2/0063
See application file for complete search history.

(56) References Cited

U.S. PATENT DOCUMENTS

| 511,238 A | 12/1893 | Hieatzman et al. |
| 765,793 A | 7/1904 | Ruckel |
| 1,728,316 A | 9/1929 | Von Wachenfeldt |
| 1,855,546 A | 4/1932 | File |
| 1,868,100 A | 7/1932 | Goodstein |

(Continued)

FOREIGN PATENT DOCUMENTS

| CA | 2390508 A1 | 5/2001 |
| EP | 0142225 A1 | 5/1985 |

(Continued)

OTHER PUBLICATIONS

"Rotator Cuff Tear," Wikipedia, the free encyclopedia, 14 pages, Downloaded on Dec. 6, 2012.

(Continued)

*Primary Examiner* — Dinah Baria
(74) *Attorney, Agent, or Firm* — Seager, Tufte & Wickhem LLP.

(57) ABSTRACT

A tendon repair implant for treatment of a complete or partial thickness tear in the supraspinatus tendon of the shoulder is provided. The implant may incorporate features of rapid deployment and fixation by arthroscopic means that compliment current procedures; tensile properties that result in desired sharing of anatomical load between the implant and native tendon during rehabilitation; selected porosity and longitudinal pathways for tissue in-growth; sufficient cyclic straining of the implant in the longitudinal direction to promote remodeling of new tissue to tendon-like tissue; and, may include a bioresorbable construction to provide transfer of additional load to new tendon-like tissue and native tendon over time.

21 Claims, 10 Drawing Sheets

(56) References Cited

U.S. PATENT DOCUMENTS

| | | |
|---|---|---|
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,570,497 A | 10/1951 | Senderowitz |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gattuma |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gattuma et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,171,273 A | 12/1992 | Silver et al. |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |

(56) References Cited

U.S. PATENT DOCUMENTS

| | | |
|---|---|---|
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,286 B2 | 7/2003 | Campin et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,702,215 B2 | 3/2004 | Stamm et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |

(56) References Cited

U.S. PATENT DOCUMENTS

| | | |
|---|---|---|
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 8,801,801 B2 | 8/2014 | Datta et al. |
| 8,821,537 B2 | 9/2014 | Euteneuer et al. |
| 8,864,780 B2 | 10/2014 | Euteneuer et al. |
| 9,033,201 B2 | 5/2015 | Euteneuer |
| 9,095,337 B2 | 8/2015 | Euteneuer et al. |
| 9,101,460 B2 | 8/2015 | Euteneuer et al. |
| 9,107,661 B2 | 8/2015 | Euteneuer et al. |
| 9,113,977 B2 | 8/2015 | Euteneuer et al. |
| 9,125,650 B2 | 9/2015 | Euteneuer et al. |
| 9,198,751 B2 | 12/2015 | Euteneuer et al. |
| 9,204,940 B2 | 12/2015 | Euteneuer et al. |
| 9,247,978 B2 | 2/2016 | Euteneuer et al. |
| 9,271,726 B2 | 3/2016 | Euteneuer |
| 9,314,314 B2 | 4/2016 | Euteneuer et al. |
| 9,314,331 B2 | 4/2016 | Euteneuer et al. |
| 9,370,356 B2 | 6/2016 | Euteneuer et al. |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0138705 A1 | 7/2004 | Heino et al. |
| 2004/0167519 A1 | 8/2004 | Weiner et al. |
| 2004/0267277 A1 | 12/2004 | Zannis et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0113938 A1 | 5/2005 | Jamiolkowski et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0063599 A1 | 3/2010 | Brunelle et al. |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0256777 A1 | 10/2010 | Datta et al. |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0184530 A1 | 7/2011 | Datta et al. |
| 2011/0224702 A1 | 9/2011 | Van Kampen et al. |
| 2011/0264149 A1 | 10/2011 | Pappalardo et al. |
| 2012/0029537 A1 | 2/2012 | Mortarino |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |
| 2012/0248171 A1 | 10/2012 | Bailly et al. |
| 2012/0316608 A1 | 12/2012 | Foley |
| 2013/0153627 A1 | 6/2013 | Euteneuer et al. |
| 2013/0153628 A1 | 6/2013 | Euteneuer |
| 2013/0158554 A1 | 6/2013 | Euteneuer et al. |
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |

(56) References Cited

U.S. PATENT DOCUMENTS

| | | | |
|---|---|---|---|
| 2014/0371853 A1 | 12/2014 | Kampen et al. | |
| 2015/0313705 A1 | 11/2015 | Euteneuer et al. | |
| 2016/0228608 A1 | 8/2016 | Hakimi et al. | |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |
| EP | 2030576 A2 | 3/2009 |
| GB | 2154688 A | 9/1985 |
| GB | 2397240 A | 7/2004 |
| JP | 58188442 A | 11/1983 |
| JP | 2005586122 A | 3/2005 |
| JP | 2006515774 A | 6/2006 |
| WO | 8505025 A1 | 11/1985 |
| WO | 0176456 A2 | 10/2001 |
| WO | 0234140 A2 | 5/2002 |
| WO | 2003105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2010081029 A1 | 7/2010 |
| WO | 2011095890 A2 | 8/2011 |
| WO | 2011128903 A2 | 10/2011 |

OTHER PUBLICATIONS

Alexander et al., "Ligament and tendon repair with an absorbable polymer-coated carbon fiber stent," Bulletin of the Hospital for Joint Diseases Orthopaedic Institute, 46(2):155-173, 1986.

Bahler et al., "Trabecular bypass stents decrease intraocular pressure in cultured himan anterior segments," Am. J. Opthamology, 138(6):988-994, Dec. 2004.

Chamay et al., "Digital contracture deformity after implantation of a silicone prosthesis: Light and electron microscopic study," The Journal of Hand Surgery, 3(3):266-270, May 1978.

D'Ermo et al., "Our results of the operation of ab externo," Opthalmologica, 168: 347-355, 1971.

Finnan et al., "Partial-thickness rotator cuff tears," J. Shoulder Elbow Surg. vol. 19: 609-616, 2010.

France et al., "Biomechanical evaluation of rotator cuff fixation methods," The American Journal of Sports Medicine, 17(2), 1989.

Goodship et al., "An assessment of filamentous carbon fibre for the treatment of tendon injury in the horse," Veterinary Record, 106: 217-221, Mar. 8, 1980.

Hunter et al., "Flexor-tendon reconstruction in severely damaged hands," The Journal of Bone and Joint Surgery (American Volume), 53-A(5): 329-358, Jul. 1971.

Johnstone et al., "Microsurgery of Schlemm's canal and the human aqueous outflow system," Am. J. Opthamology, 76(6): 906-917, Dec. 1973.

Kowalsky et al., "Evaluation of suture abrasion against rotator cuff tendon and proximal humerus bone," Arthroscopy: The Journal of Arthroscopic and Related Surgery, 24(3):329-334, Mar. 2008.

Lee et al., "Aqueous-venous and intraocular pressure. Preliminary report of animal studies," Investigative Opthalmology, 5(1): 59-64, Feb. 1966.

Maepea et al., "The pressures in the episcleral veins, Schlemm's canal and the trabecular meshwork in monkeys: Effects of changes in intraocular pressure," Exp. Eye Res., 49:645-663, 1989.

Nicolle et al., "A silastic tendon prosthesis as an adjunct to flexor tendon grafting: An experimental and clinical evaluation," British Journal of Plastic Surgery, 22(3-4):224-236, 1969.

Rubin et al., "The use of acellular biologic tissue patches in foot and ankle surgery," Clinics in Podiatric Medicine and Surgery, 22:533-552, 2005.

Schultz, "Canaloplasty procedure shows promise for open-angle glaucoma in European study," Ocular Surgery News, 34-35, Mar. 1, 2007.

Spiegel et al., "Schlemm's canal implant: a new method to lower intraocular pressure in patients with POAG," Opthalmic Surgery and Lasers, 30(6):492-494, Jun. 1999.

Stenson et al., "Arthroscopic treatment of partial rotator cuff tears," Operative Techniques in Sports Medicine, 12(2):135-148, Apr. 2004.

Valdez et al., "Repair of digital flexor tendon lacerations in the horse, using carbon fiber implants," JAYMA, 177(5): 427-435, Sep. 1, 1980.

Zobitz et al., "Determination of the compressive materials properties of the supraspinatus tendon," J. Biomech. Eng., vol. 123(1): Feb. 2001.

Notification of Transmittal of the International Search Report and the Written Opinion of the International Searching Authority, or the Declaration for Application No. PCT/US2016/037354, 2016, 11 pages, dated Aug. 25, 2016.

TENDON REPAIR IMPLANT AND METHOD OF IMPLANTATION

CROSS REFERENCE TO RELATED APPLICATIONS

This application claims the benefit of U.S. Provisional Patent Application Ser. No. 62/175,829 filed on Jun. 15, 2015, the disclosure of which is incorporated herein by reference.

TECHNICAL FIELD

The present disclosure pertains generally, but not by way of limitation, to orthopedic implants and methods of treatment. More particularly, the present invention relates to a tendon repair implant, such as one that is engineered for arthroscopic placement over or in the area of a full thickness tear of the supraspinatus tendon of the shoulder

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. The accepted treatment for a full thickness rotator cuff tear includes reattaching the torn tendon to the humeral head using sutures. In treating large or massive full thickness tears, accepted practice also can include the placement of scaffolds and patches over the repaired tendon to mechanically augment the strength of the repaired tendon.

For partial thickness rotator cuff tears, and for full thickness tears that do not require mechanical augmentation, a bioinductive implant has been used to induce new tendinous tissue, which biologically augments the tendon and enables healing of partial thickness defects, as well as improved reattachment of full thickness repairs to the humeral head. The healing response associated the bioinductive implant results in integration of the newly induced tissue with the native tissues, which provides a biological connection for load sharing that is not dependent on sutures or some other mechanical anchor or connector. This biological connection is a critically important aspect of biological augmentation because long-term load sharing is not dependent on sutures, which may migrate through the tissues, but is ensured by the continuity of the collagen fibers in the induced tissue with native tissues. The bioinductive implant, however, does not provide any immediate mechanical augmentation; rather, the newly induced tissue provides biological augmentation over time.

Current scaffolds or patches used to augment rotator cuff repairs are designed to provide initial mechanical augmentation, i.e., added strength, at the time of surgery. Use of these implants, however, often do not provide any benefit beyond the immediate postoperative period. Thus, there is a need for an implant that not only provides initial mechanical augmentation, but also provides improved healing.

BRIEF SUMMARY

In accordance with aspects of the disclosure, a tendon repair implant is provided that combines the benefits of a bioinductive implant, which biologically augments a repaired tendon and improves healing, with an implant that provide mechanical augmentation for added strength in the early postoperative period. An example tendon repair implant comprises a sheet-like structure including a first component configured to have an initial tensile modulus of about 5 megapascals (MPa) to 50 MPa and comprising a plurality of pores for tissue in-growth and a second component configured to have an initial tensile modulus of about 50 MPa to 150 MPa; wherein the sheet-like structure conforms to the surface of the tendon and is configured to have an initial load share representing about 50% or more of the load of the tendon when affixed to the tendon.

Alternatively or additionally to the above example, in another example, the first component and the second component form discrete layers.

Alternatively or additionally to the examples above, in another example, the second component is intermixed with the first component to form a composite material.

Alternatively or additionally to the examples above, in another example, about 50% or more of the load of the tendon comprises between 25 Newtons (N) and 50 N.

Alternatively or additionally to the examples above, in another example, the sheet-like structure is configured to degrade in tensile strength from an initial tensile strength thereby sharing less of the load of the tendon over time but retain at least about 50% of the initial load share of the sheet-like implant three months after being affixed to the tendon.

Alternatively or additionally to the examples above, in another example, wherein to retain at least about 50% of the initial load share of the sheet-like implant at three months, the sheet-like structure is configured to retain at least about 70% of the initial tensile strength three months after being affixed to the tendon and to retain at least about 50% of the initial tensile strength and about 50% of an initial compressive modulus three months after being affixed to the tendon.

Alternatively or additionally to the examples above, in another example, the first component is configured to degrade in tensile strength from an initial tensile strength at a first rate and the second component is configured to degrade in tensile strength from an initial tensile strength at a second rate different from the first rate.

Alternatively or additionally to the examples above, in another example, the second rate is slower than the first rate.

Alternatively or additionally to the examples above, in another example, the first component comprises a bioresorbable material.

Alternatively or additionally to the examples above, in another example, the second component comprises a bioresorbable material.

Alternatively or additionally to the examples above, in another example, the first component comprises a polymer material.

Alternatively or additionally to the examples above, in another example, the second component comprises a polymer material.

Alternatively or additionally to the examples above, in another example, the sheet-like structure is further configured to be attached to the surface of the tendon without significant pre-loading or significant pre-stretching.

Alternatively or additionally to the examples above, in another example, the sheet-like structure has one or more agents affixed thereto which promote tissue in-growth.

Alternatively or additionally to the examples above, in another example, the pores have sizes between about 20 microns and 400 microns.

Alternatively or additionally to the examples above, in another example, the sheet-like structure is defined by a longitudinal dimension, a lateral dimension, and a thickness dimension, wherein the longitudinal dimension is greater than the lateral dimension and the thickness dimension, and wherein the sheet-like structure further comprises one or more longitudinal pathways extending along the longitudinal dimension of the sheet-like structure.

Alternatively or additionally to the examples above, in another example, the sheet-like structure has a maximum of about 0.5% creep over three months.

Alternatively or additionally to the examples above, in another example, further comprising a third component configured to have an initial tensile modulus of about 5 MPa to 50 MPa.

Another example tendon repair implant comprises a sheet-like structure including a first component configured to have an initial tensile modulus of about 5 megapascals (MPa) to 20 MPa and comprising a plurality of pores for tissue in-growth and a second component configured to have an initial tensile modulus of about 20 MPa to 50 MPa; wherein the sheet-like structure conforms to the surface of the tendon and is configured to have an initial load share representing about 10% to 50% of the load of the tendon when affixed to the tendon.

Alternatively or additionally to the examples above, in another example, the first component and the second component form discrete layers.

Alternatively or additionally to the examples above, in another example, the second component is intermixed with the first component to form a composite material.

Alternatively or additionally to the examples above, in another example, about 10% to 50% the load of the tendon comprises between 5 Newtons (N) and 25 N.

Alternatively or additionally to the examples above, in another example, the sheet-like structure is configured to degrade in tensile strength from an initial tensile strength thereby sharing less of the load of the tendon over time but retain at least about 50% of the initial load share of the sheet-like implant three months after being affixed to the tendon.

Alternatively or additionally to the examples above, in another example, to retain at least about 50% of the initial load share of the sheet-like implant at three months, the sheet-like structure is configured to retain at least about 70% of the initial tensile strength three months after being affixed to the tendon and to retain at least about 50% of the initial tensile strength and about 50% of an initial compressive modulus three months after being affixed to the tendon.

Alternatively or additionally to the examples above, in another example, the first component is configured to degrade in tensile strength from an initial tensile strength at a first rate and the second component is configured to degrade in tensile strength from an initial tensile strength at a second rate different from the first rate.

Alternatively or additionally to the examples above, in another example, the second rate is slower than the first rate.

Alternatively or additionally to the examples above, in another example, the first component comprises a bioresorbable material.

Alternatively or additionally to the examples above, in another example, the second component comprises a bioresorbable material.

Alternatively or additionally to the examples above, in another example, the first component comprises a polymer material.

Alternatively or additionally to the examples above, in another example, the second component comprises a polymer material.

Alternatively or additionally to the examples above, in another example, the sheet-like structure is further configured to be attached to the surface of the tendon without significant pre-loading or significant pre-stretching.

Alternatively or additionally to the examples above, in another example, the sheet-like structure has one or more agents affixed thereto which promote tissue in-growth.

Alternatively or additionally to the examples above, in another example, the pores have sizes between about 20 microns and 400 microns.

Alternatively or additionally to the examples above, in another example, the sheet-like structure is defined by a longitudinal dimension, a lateral dimension, and a thickness dimension, wherein the longitudinal dimension is greater than the lateral dimension and the thickness dimension, and wherein the sheet-like structure further comprises one or more longitudinal pathways extending along the longitudinal dimension of the sheet-like structure.

Alternatively or additionally to the examples above, in another example, the sheet-like structure has a maximum of about 0.5% creep over three months.

Alternatively or additionally to the examples above, in another example, further comprising a third component configured to have an initial tensile modulus of about 20 MPa to 50 MPa.

Another example tendon repair implant for repair of a complete or partial thickness tear of a supraspinatus tendon having a load bearing direction, the tendon repair implant comprises a sheet-like structure having a longitudinal dimension, a lateral dimension, and a thickness dimension and configured to be affixed to a surface of the supraspinatus tendon such that the longitudinal dimension of the sheet-like structure extends generally parallel to the load bearing direction of the supraspinatus tendon, the sheet-like structure including a first component configured to have an initial tensile modulus of about 5 megapascals (MPa) to 50 MPa and comprising a plurality of pores for tissue in-growth and a plurality of longitudinal pathways that encourage tissue in-growth therein, wherein the longitudinal pathways extend along the longitudinal dimension of the sheet-like structure and have cross sections of about 150 microns to 200 microns and a second component configured to have an initial tensile modulus of about 50 MPa to 150 MPa; wherein when affixed to the surface of the supraspinatus tendon, the sheet-like structure is configured to initially share about 50% or more of a load applied to the supraspinatus tendon.

Alternatively or additionally to the examples above, in another example, the first component and the second component form discrete layers.

Alternatively or additionally to the examples above, in another example, the second component is intermixed with the first component to form a composite material.

Alternatively or additionally to the examples above, in another example, the pores range in size from about 20 to 400 microns.

Another example tendon repair implant for repair of a complete or partial thickness tear of a supraspinatus tendon having a load bearing direction, the tendon repair implant comprises a sheet-like structure having a longitudinal dimension, a lateral dimension, and a thickness dimension and configured to be affixed to a surface of the supraspinatus tendon such that the longitudinal dimension of the sheet-like structure extends generally parallel to the load bearing direction of the supraspinatus tendon, the sheet-like structure including a first component configured to have an initial tensile modulus of about 5 megapascals (MPa) to 20 MPa and comprising a plurality of pores for tissue in-growth and a plurality of longitudinal pathways that encourage tissue in-growth therein, wherein the longitudinal pathways extend along the longitudinal dimension of the sheet-like structure and have cross sections of about 150 microns to 200 microns and a second component configured to have an initial tensile modulus of about 20 MPa to 50 MPa; wherein when affixed to the surface of the supraspinatus tendon, the sheet-like structure is configured to have an initial load share representing about 10% to 50% of a load applied to the supraspinatus tendon.

Alternatively or additionally to the examples above, in another example, the first component and the second component form discrete layers.

Alternatively or additionally to the examples above, in another example, the second component is intermixed with the first component to form a composite material.

Alternatively or additionally to the examples above, in another example, the pores range in size from about 20 to 400 microns.

An example method for manufacturing a tendon repair implant for repair of a complete or partial thickness tear of a tendon comprises rotating a mandrel at a first speed; collecting a plurality of fibers on the rotating mandrel at the first speed; after collecting a plurality of fibers on the rotating mandrel at the first speed, rotating the mandrel at a second speed, different than the first speed; and collecting a plurality of fibers on the rotating mandrel at the second speed.

The above summary of some examples and embodiments is not intended to describe each disclosed embodiment or every implementation of the present disclosure. The Brief Description of the Drawings, and Detailed Description, which follow, more particularly exemplify these embodiments, but are also intended as exemplary and not limiting.

Figure 1:
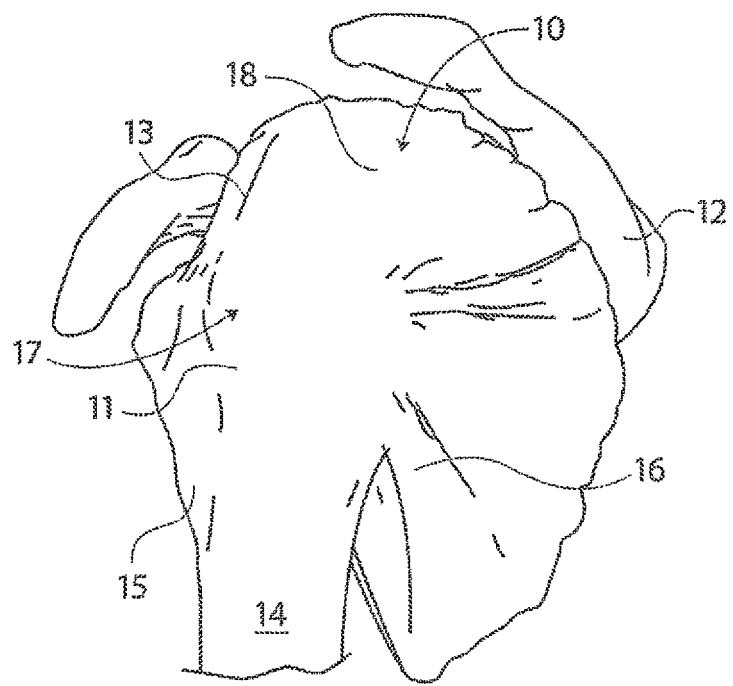
FIG. 1 is a simplified perspective view of the human rotator cuff and associated anatomical structure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or able to be arranged with each other to form other additional embodiments or to complement and/or enrich the described embodiment(s), as would be understood by one of ordinary skill in the art.

As disclosed by Ball et al. in U.S. Patent Publication No. US 2008/0188936 A1 and as illustrated in FIG. 1, the rotator cuff 10 is the complex of four muscles that arise from the scapula 12 and whose tendons blend in with the subjacent capsule as they attach to the tuberosities of the humerus 14.

The subscapularis 16 arises from the anterior aspect of the scapula 12 and attaches over much of the lesser tuberosity. The supraspinatus muscle 18 arises from the supraspinatus fossa of the posterior scapula, passes beneath the acromion and the acromioclavicular joint, and attaches to the superior aspect of the greater tuberosity 11. The infraspinatus muscle 13 arises from the infraspinous fossa of the posterior scapula and attaches to the posterolateral aspect of the greater tuberosity 11. The teres minor 15 arises from the lower lateral aspect of the scapula 12 and attaches to the lower aspect of the greater tuberosity 11. Proper functioning of the rotator depends on the fundamental centering and stabilizing role of the humeral head 15 with respect to sliding action during anterior and lateral lifting and rotational movements of the arm.

The insertion of these tendons as a continuous cuff 10 around the humeral head 17 permits the cuff muscles to provide an infinite variety of moments to rotate the humerus 14 and to oppose unwanted components of the deltoid and pectoralis muscle forces. The insertion of the infraspinatus 13 overlaps that of the supraspinatus 18 to some extent. Each of the other tendons 16, 15 also interlaces its fibers to some extent with its neighbor's tendons. The tendons splay out and interdigitate to form a common continuous insertion on the humerus 14.

The rotator cuff muscles 10 are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

The mechanics of the rotator cuff 10 are complex. The cuff muscles 10 rotate the humerus 14 with respect to the scapula 12, compress the humeral head 17 into the glenoid fossa providing a critical stabilizing mechanism to the shoulder (known as concavity compression), and provide muscular balance. The supraspinatus and infraspinatus provide 45 percent of abduction and 90 percent of external rotation strength. The supraspinatus and deltoid muscles are equally responsible for producing torque about the shoulder joint in the functional planes of motion.

Figure 2:
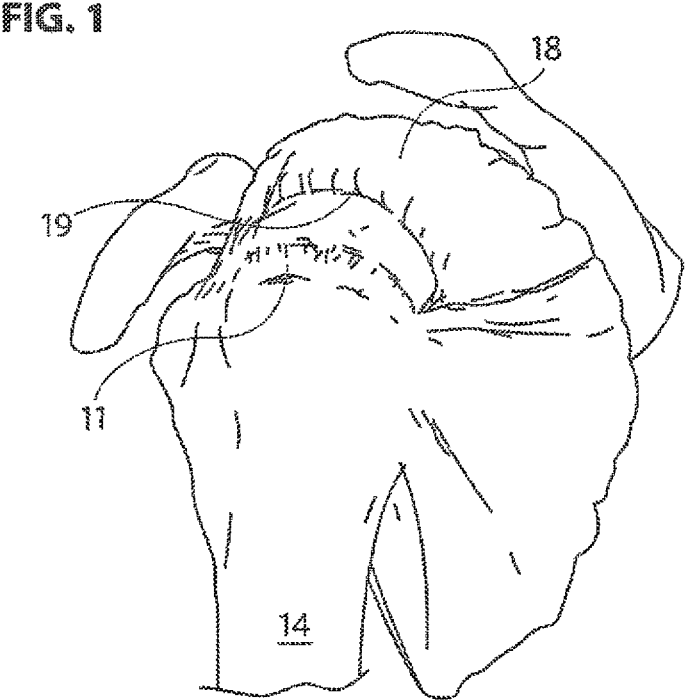
FIG. 2 is a schematic depiction of a full thickness tear in the supraspinatus tendon of the rotator cuff of FIG. 1.

With its complexity, range of motion and extensive use, a fairly common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear in the supraspinatus tendon 19 is schematically depicted in FIG. 2. A tear at the insertion site of the tendon with the humerus, may result in the detachment of the tendon from the bone. This detachment may be partial or full, depending upon the severity of the injury. Additionally, the strain or tear can occur within the tendon itself. Injuries to the supraspinatus tendon 19 and recognized modalities for treatment are defined by the type and degree of tear. The first type of tear is a full thickness tear as also depicted in FIG. 2, which as the term indicates is a tear that extends through the thickness of the supraspinatus tendon regardless of the width of the tear. The second type of tear is a partial thickness tear which is further classified based on how much of the thickness is torn whether it is greater or less than 50% of the thickness.

The accepted treatment for a full thickness tear or a partial thickness tear greater than 50% includes reattaching the torn tendon to the humeral head using sutures. For the partial thickness tears greater than 50%, the tear is often completed to a full thickness tear by cutting the tendon prior to reattachment of the tendon. In treating a full thickness tear or partial thickness tear of greater than 50% after completing the tear by cutting the tendon, accepted practice also can include the placement of scaffolds and patches over the repaired tendon to shield the sutured or repaired tendon area from anatomical load during rehabilitation. For example, Wright Medical discloses that the GraftJacket® can be used to augment a suture repaired tendon in large and massive full thickness tears or smaller full-thickness tears in a shoulder having severely degenerated tissue. However, it is recognized that excessive shielding of the tendon from load can lead to atrophy and degeneration of the native tendon.

It is known that, for the rotator cuff, allowing the tendon to experience full anatomical load during recovery after repairing the tendon tear with sutures will result in a 20-60% failure rate. Ball et al. (US Patent Appl. Pub. No. 2008/0188936 A1) disclose an implant that provides a healing modality that shields the tendon from most of the anatomical loads in the early part of the recovery period, and gradually experience increasing loads as the repair heals to full strength. Ball et al. disclose the strength of the surgical repair, expressed as percent strength of the final healed repair, begins post-surgically at the strength of the suture-to-tissue connection alone. In their illustrated example, the suture-to-tissue connection represents about 25% of the strength. The augmentation implant initially receives the 75% of the loads experienced during recovery through high initial strength. Gradually, the ratio of load sharing shifts to the suture-to-tissue connection as the repair heals and gains strength, while the implant is simultaneously absorbed by the body. Strength retention is defined to refer to the amount of strength that a material maintains over a period of time following implantation into a human or animal. For example, if the tensile strength of an absorbable mesh or fiber decreases by half over three months when implanted into an animal or human, the mesh or fiber's strength retention at 3 months would be 50%.

However, some implants may not provide biological continuity between the implant and the tendon. For example, the suture connection may be the only means to off-load the tendon. It is contemplated that the implant may not carry any load if mechanical "conditioning" does not remove slack in the implant. Further, soon after surgery, if the sutures slip through the tissue, even slightly, the ability to off-load the tendon may be lost. Creep/stress relaxation may also limit the ability of the implant to carry the load long-term. Strain in the tendon is about 2% under normal loads, so an implant creep of only about 2% may completely eliminate the ability of the implant to provide augmentation). In some instances, the implant may not support or encourage tissue ingrowth. As a result, the implant may be incapable of remodeling and therefore cannot adapt to changing demands as rehabilitation progresses. These drawbacks of current implants are overcome by the current invention, which induces new tendinous tissue that integrates with the native tissues, providing continuity between the structures that is not dependent on mechanical connections for load sharing.

Figure 3:
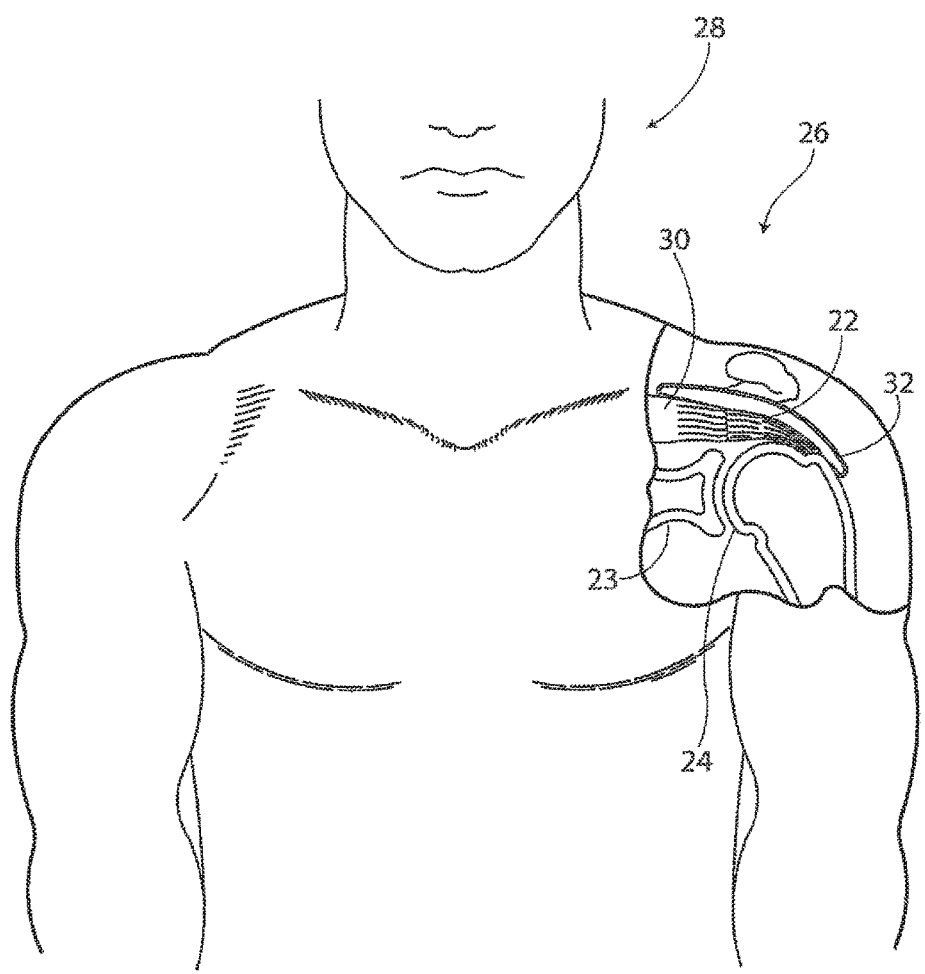
FIG. 3 is an anterior view showing the upper torso of a patient with the left shoulder shown in cross-section.

FIG. 3 is a stylized anterior view of a patient 28. For purposes of illustration, a shoulder 26 of patient 28 is shown in cross-section in FIG. 3. Shoulder 26 includes a humerus 24 and a scapula 23. The movement of humerus 24 relative to scapula 23 is controlled by the muscles of the rotator cuff as previously discussed with respect to FIG. 1. For purposes of illustration, only the supraspinatus 30 is shown in FIG. 3. With reference to FIG. 3, it will be appreciated that a distal tendon 22 of the supraspinatus 30 (hereinafter referred to as the supraspinatus tendon) meets humerus 24 at an insertion point 32.

Figure 4:
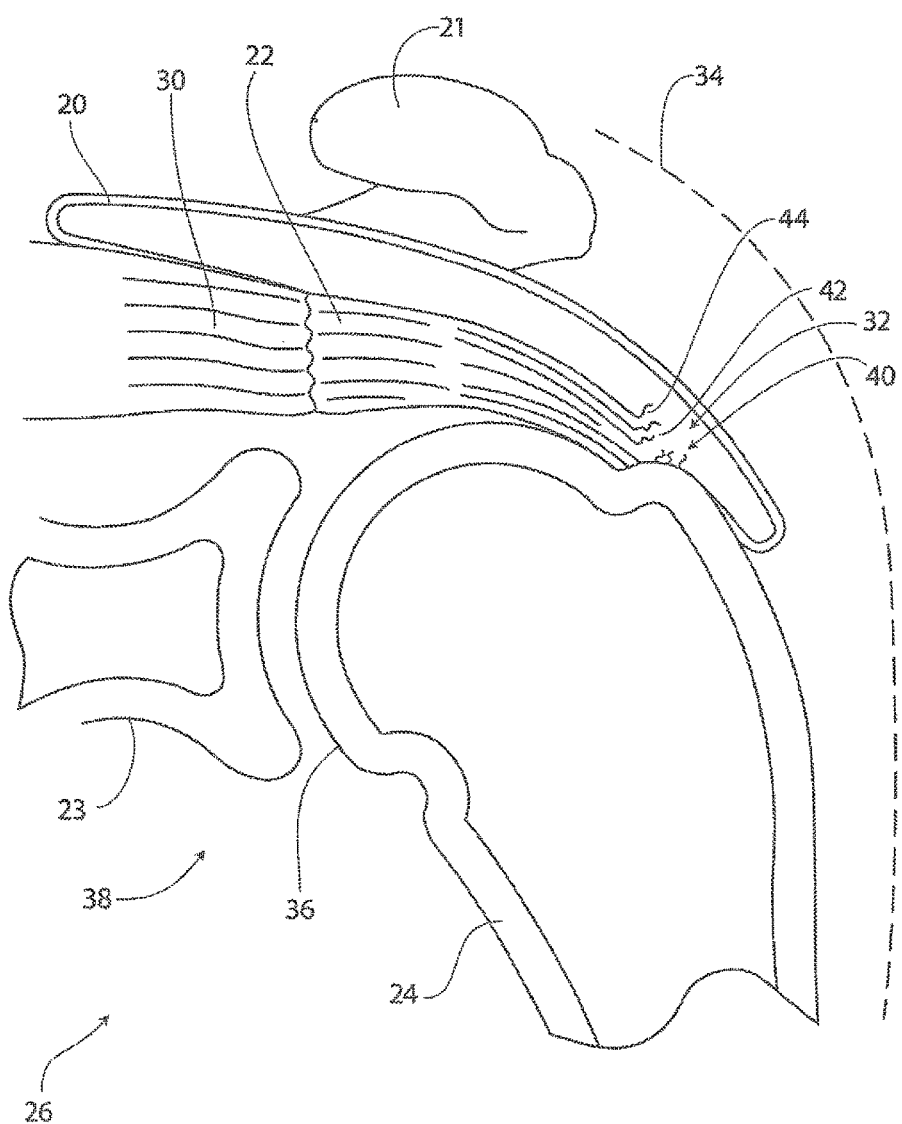
FIG. 4 is an enlarged, cross-sectional view showing the left shoulder depicted in FIG. 3.

FIG. 4 is an enlarged cross sectional view of shoulder 26 shown in the previous figure. In FIG. 4, a head 36 of humerus 24 is shown mating with a glenoid fossa of scapula 23 at a glenohumeral joint 38. The glenoid fossa comprises a shallow depression in scapula 23. A supraspinatus 30 and a deltoid 34 are also shown in FIG. 4. These muscles (along with others) control the movement of humerus 24 relative to scapula 23. A distal tendon 22 of supraspinatus 30 meets humerus 24 at an insertion point 32. In the embodiment of FIG. 4, tendon 22 includes a damaged portion 40 located near insertion point 32. Damaged portion 40 includes a tear 42 extending partially through tendon 22. Tear 42 may be referred to as a partial thickness tear. The depicted partial thickness tear is on the bursal side of the tendon; however, the tear can be on the opposite or articular side of the tendon or may include internal tears to the tendon not visible on either surface. Tendon 22 of FIG. 4 has become frayed. A number of loose tendon fibers 44 are visible in FIG. 4.

Scapula 23 includes an acromion 21. In FIG. 4, a subacromial bursa 20 is shown extending between acromion 21 of scapula 23 and head 36 of humerus 24. In FIG. 4, subacromial bursa 20 is shown overlaying supraspinatus 30. Subacromial bursa 20 is one of more than 150 bursae found the human body. Each bursa comprises a fluid filled sac. The presence of these bursae in the body reduces friction between bodily tissues.

Figure 5:
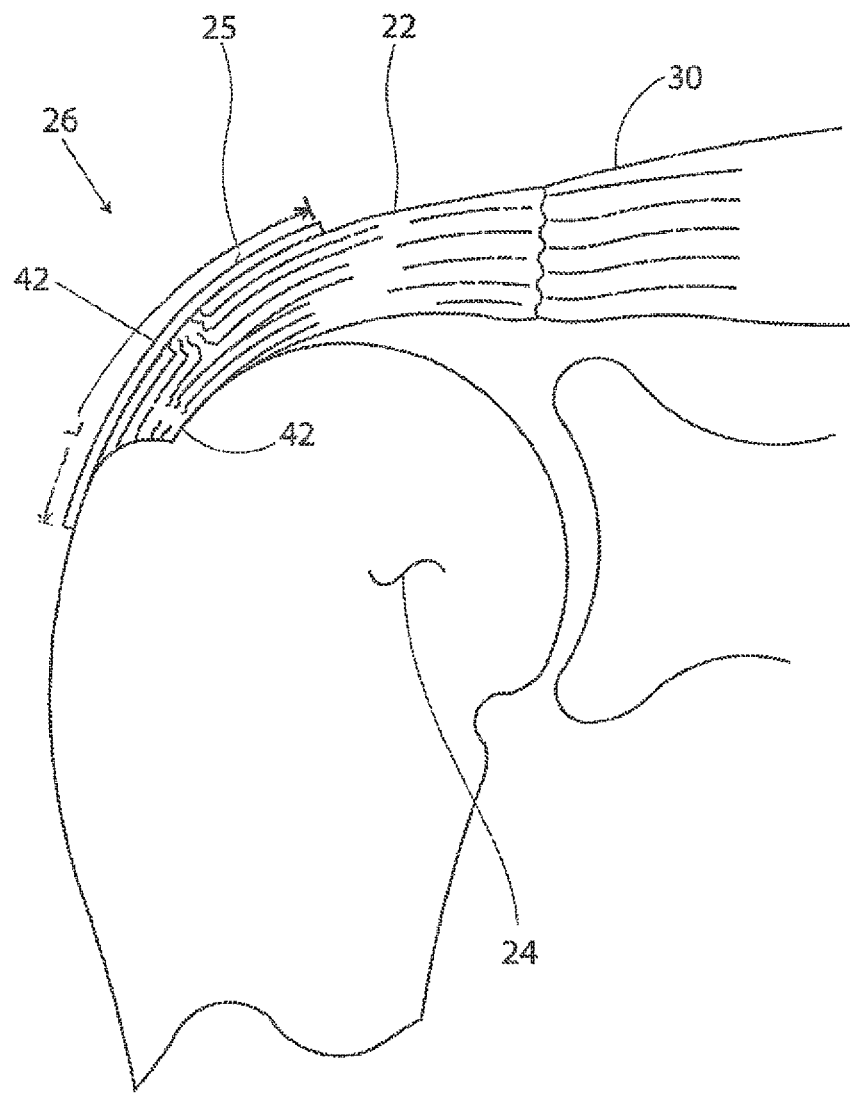
FIG. 5 is an enlarged schematic cross-sectional view of a shoulder showing partial thickness tears and an exemplary tendon repair implant positioned thereon.

FIG. 5 is an additional cross sectional view of shoulder 26 shown in the previous figure. In the embodiment of FIG. 5, a tendon repair implant 25 has been placed over the partial thickness tear 42. In this embodiment, the tendon repair implant 25 is placed on the bursal side of the tendon regardless of whether the tear is on the bursal side, articular side or within the tendon. Further, the tendon repair implant may overlay multiple tears, as an articular sided tear is also shown in FIG. 5.

In some embodiments, the tendon repair implant is engineered to provide a combination of structural features, properties and functions that are particularly appropriate for treating a full thickness tear or a partial thickness tear of greater than 50%, without physically cutting, then suturing the tendon, as is typically done in treating full thickness tears or partial thickness tears greater than 50%. While the tendon repair implant 25 is described with respect to full thickness tears or a partial thickness tear of greater than 50%, it is contemplated that the implant 25 may also be used in a partial thickness tear of less than 50%. These features may include: rapid deployment and fixation by arthroscopic means that compliment current procedures; tensile properties that result in desired sharing of anatomical load between the implant and native tendon during rehabilitation; selected porosity and longitudinal pathways for tissue in-growth; sufficient cyclic straining of the implant, having new tissue in-growth, in the longitudinal direction to promote remodeling of new tissue to tendon-like tissue; induction of a healing response; and, the tendon repair implant is bioabsorbable or otherwise absorbable to provide transfer of additional load to native tendon over time.

In some embodiments, tendon repair implants are structured for rapid deployment and fixation by arthroscopic means to complement current techniques used to relieve impingement or restricted movement of tendon relative to bone, such as acromioplasty and tunneling procedures in partial thickness tear treatments. The tendon repair implant 25 is a generally sheet-like structure that has a surface that conforms to the tendon surface when implanted. Further, the physical properties of the implant may be such that no significant prestretching or pre-loading of the implant during placement is required for it to function in sharing a sufficient portion of the anatomical load with the native tendon, as discussed below. Stated another way, the tensile properties of the implant may be designed to share a sufficient portion of the anatomical load present during rehabilitation by laying the implant in surface to surface contact with the tendon without any significant wrinkles. Therefore, the tendon repair implant may be delivered in a folded, rolled or other reduced configuration through an arthroscopic instrument and spread out into the sheet-like shape with its surface in contact and generally conforming to the tendon surface without significant stretching before fixation to the tendon. Fixation may be accomplished via arthroscopic suturing or stapling techniques.

Current procedures for repairing full thickness tears or partial thickness tears greater than 50% include cutting and suturing of the tendon itself and may include the addition of an implant that is designed to shield the tendon repair area from experiencing stresses during use. With current stress shielding implants, the concern is the strain and load at which the implant versus the suture repair fails, as the goal is to prevent suture failure during excessive loading. In contrast, the tendon repair implants in some embodiments of the present disclosure have tensile properties to selectively share the anatomical load between damaged native tendon and the implant during the normal range of strains experienced during rehabilitation.

The tensile properties of some tendon repair implants described in the present disclosure are engineered to selectively share the anatomical load during rehabilitation. As installed over the damaged tendon, the tendon repair implant 25 and native tendon 22 are two generally parallel structures that each carry a portion of a load generated by contraction of the supraspinatus muscle 30. The relative load carried by each depends on the tensile properties of the each structure. As parallel structures, the tendon repair implant 25 and the native tendon 22 each experience similar strain under a given load, depending on the effectiveness of the attachment between the tendon and the implant. It is known that native tendon will fail at strains of about 8%, and in normal use tendons experience less than 5% strain. During rehabilitation after surgery, the native tendon is exposed to strains of about 0% to 3%. In some embodiments, tendon repair implants of the present disclosure are engineered with tensile properties in the range of 1% to 3% strain in order to properly share anatomical load during rehabilitation, as this is the range over which tensile properties affect the function of the implant. The tensile modulus of the implant relative to the tensile modulus of the tendon determines the load carried by the implant, i.e., the amount of load sharing. In some embodiments, the tensile modulus of the implant ranges from about 5 megapascals (MPa) to about 150 MPa in the range of 1% to 3% strain. In some embodiments, the tensile modulus of the implant may be about 20 to about 100 MPa in the range of 1% to 3% strain. The modulus value for a given material may be calculated from a best fit linear regression for data collected over the range of 1% to 3% strain. Depending upon the properties of the native tendon to which the implant is attached, this may result in initial load sharing following surgery with about 50% or more being carried by the implant. In some embodiments, about 10% to about 50% of the load may be carried by the implant. The load on the supraspinatus tendon during rehabilitation may be about 50 Newtons (N) to about 100 N, translating to a load on the implant of about 10 N to about 50 N. The tensile modulus can be measured with a 1 N preload at zero strain and elongation rate of 1% per second after positioning the sheet-like structure in a generally flat and non-wrinkled format.

In some embodiments, a tendon repair implant of the present disclosure includes a selected porosity and longitudinal pathways for tissue in-growth. In some useful embodiments, the sheet-like structure of the implant comprises a material defining a plurality of pores that encourage tissue growth therein. The porosity and tissue in-growth allows for new collagen to integrate with collagen of the native tendon for functional load carrying. A coating that encourages tissue growth or in-growth may be applied to the surfaces of the sheet-like structure. It will be appreciated that sheet-like structure may comprise various pore defining structures without deviating from the spirit and scope of the present description. In some embodiments, the sheet-like structure has a pore size in the range of about 20 to about 400 microns. In some embodiments the pore size is in the range of about 100 microns to about 300 microns, and in some embodiments it is about 150 to about 200 microns. The porosity may be about 30% to about 90%, or it may be within the range of at least about 50% to about 80%. Examples of pore defining structures are discussed in more detail below for specific embodiments, but may include, but not be limited to open cell foam structures, mesh structures, micromachined layered structures and structures comprising a plurality of fibers. In some embodiments, the fibers may be interlinked with one another. Various processes may be used to interlink the fibers with one another. Examples of processes that may be suitable in some applications include weaving, knitting, and braiding.

Tendon repair implants of the present invention may have a porosity greater than 50%, however, the porosity may be further structured to include tissue in-growth pathways in the longitudinal direction of the implant. Pathways may be included to extend through the thickness of the implant or laterally in the plane of the implant. Pathways may include segments extending longitudinally in the plane of the implant. In some embodiments, longitudinally extending pathways comprise a majority of the porosity with such pathway segments having cross sections of about 150 to about 200 microns. Longitudinal pathways may be open channels or lumens that extend in the longitudinal direction in the plane of the sheet-like structure when laying flat. They may be defined in the thickness of the sheet in the longitudinal direction. Further, these longitudinal pathways may generally be maintained when the implant is subjected to longitudinal loads experienced during rehabilitation.

A tendon repair implant may include tensile properties that allow for cyclic straining of the implant and new tissue in-growth to cause and facilitate remodeling of this new tissue to a more organized structure resembling tendon-like tissue. In some embodiments, the new tissue, based on the tensile properties of the implant, experiences tendon-like strain during rehabilitation. The tendon-like tissue, which may not be as strong as native tendon, has added load bearing strength in the longitudinal direction relative to unorganized tissue. This remodeling of tissue begins within 4 to 8 weeks after implant and continues for months. The strength of the new tissue continues to increase as collagen fibers become more oriented due to the proper strain signal resulting from the properties of the implant. To facilitate cyclic loading, the tendon repair implant may have a compressive modulus greater than the native tendon. A published value for the compressive modulus of the supraspinatus tendon is in the range of 0.02-0.09 MPa (J Biomech Eng 2001, 123:47-51). In some embodiments, the implant provided by the implantable device should have a higher compressive modulus than the tendon to prevent collapse of pores in the implant. The compressive modulus may be at least about 0.1 MPa, or at least about 0.2 MPa.

In some embodiments, the tendon repair implant is bioresorbable, biodegradable or otherwise absorbable to provide transfer of additional load to native tendon over time. By 2-3 months after implantation, the new tissue in-growth should have gained strength through remodeling and it may be desirable to transfer more load from the implant to the new tissue and native tendon combination. Absorption of the implant enables the new tissue, in combination with the native tendon, to carry all of the load and develop optimal collagen fiber alignment. Further, absorption avoids potential long-term problems with particles from non-absorbable materials. The tissue within the device implant will typically be developing and organizing during the first one to three months after implantation, so load sharing with the implant is desired in some embodiments. After three months the tissue will typically be remodeling, so the mechanical properties of portions of the implant may gradually decline to zero to enable the new tissue to be subjected to load without the implant bearing any of the load. If the implant loses modulus faster than it loses strength, then the relative loads on the implant will be less at three months than when first implanted. For example, if the modulus of the implant drops 50% to 25 MPa at three months, then 2% strain of the implant would require a stress of only about 0.5 MPa. At the same time, if the strength of the implant drops about 30% to 3.5 MPa, then the strength of the implant will be about seven times the anticipated loads at three months, compared to about five times when first implanted. Therefore, with the design criteria provided above, tensile failure of the implant during the first three months should be unlikely. Accordingly, the following specifications for degradation rate are recommended in some embodiments: an ultimate tensile strength of at least 70% strength retention at three months; tensile and compressive modulus of at least 50% strength retention at three months; and no minimum specification for strength and modulus at 6 months. The device may be designed to have a degradation profile such that it is at least 85% degraded in less than 1 to 2 years after implantation.

Cyclic creep is another design constraint to be considered in some embodiments. A strain of about 2% with a 30 millimeter (mm) long implant will result in an elongation of about only 0.6 mm. Therefore, very little cyclic creep can be tolerated in these embodiments to ensure that the implant will undergo strain with each load cycle. A test where a proposed implant design is cyclically strained to 2% at 0.5 Hertz with rest periods for 8 hours provides 9000 cycles, which likely exceeds the number of cycles experienced in three months of rehabilitation of a patient's joint. Incorporation of relaxation times should be considered in such testing. In some embodiments, a maximum of about 0.5% creep is an acceptable specification.

In some useful embodiments, the tendon repair implant comprises one or more bioabsorbable materials. Examples of bioabsorbable materials that may be suitable in some applications include those in the following list, which is not exhaustive: polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly (amino acids), poly(alphahydroxy acid) or related copolymers materials.

The tendon repair implant may be configured to allow loading and retention of biologic growth factors. The implant and/or the growth factors may be configured to controllably release the growth factors. The implant may be configured to allow transmission of body fluid to remove any degradation by-products in conjunction with a potential elution profile of biologics. The implant may also include platelet rich plasma at the time of implant or other biologic factor to promote healing and tissue formation.

A tendon repair implant of the present invention can include multiple layers or surface coatings. As implanted, the bursal side of the implant can include a layer or surface that will preferably slide against tissue without adherence. The tendon side of the implant may include a layer or coating that is more compatible with fixation to the tendon surface.

Various materials and formats may be used to produce tendon repair implants of the present invention. Each material and format is engineered to include selected material properties in the ranges discussed above. Material properties can be altered in the materials making up the sheet like structure or by altering the format or pattern of the material to adjust physical properties of the composite structure.

Figure 6A:
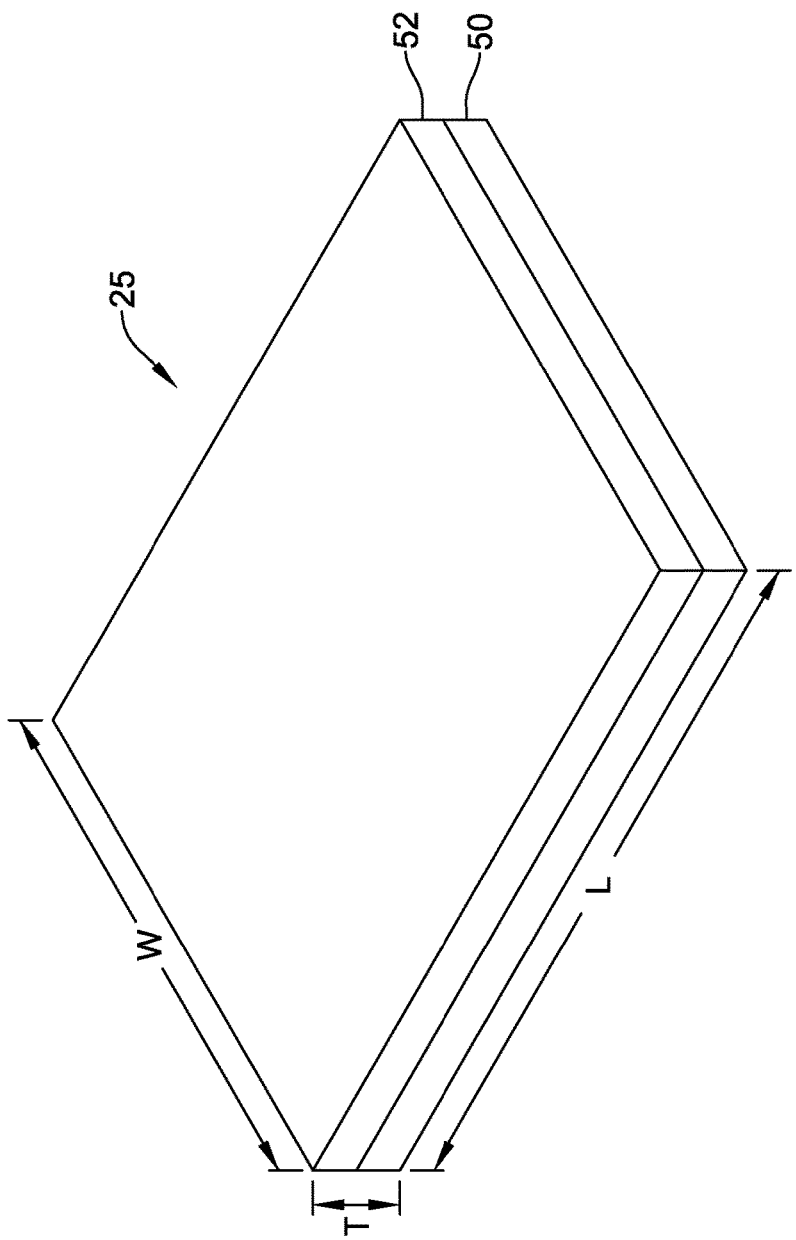
FIG. 6A is a schematic perspective view of an illustrative tendon repair implant.
Figure 6B:
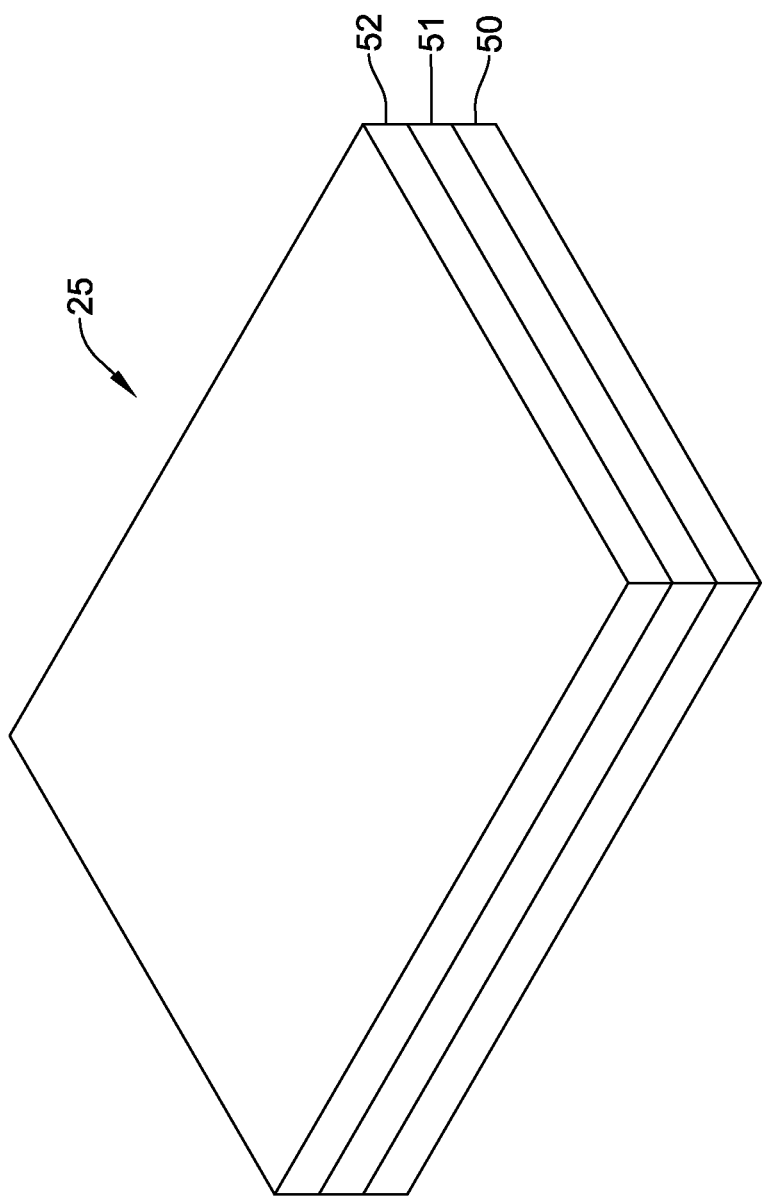
FIG. 6B is a schematic perspective view of another illustrative tendon repair implant.

FIG. 6A is a perspective, schematic view of an illustrative tendon repair implant 25. The sheet-like structure 25 is defined by a longitudinal dimension L, a lateral dimension W and a thickness T. In some embodiments, lateral and longitudinal dimensions of the implant may range from about 20 millimeters (mm) to 50 mm in the lateral direction W and 25 mm to 50 mm in the longitudinal direction L. The thickness T of the sheet-like structure may be about 1 mm to 3 mm when dehydrated. It is contemplated that the thickness of the implant 25 may be thicker, in the range of about 3 mm to 5 mm, when hydrated. Upon implantation, the longitudinal dimension L may extend generally in or parallel to the load bearing direction of the tendon. As depicted in the embodiment shown in FIG. 5, the longitudinal direction L follows the supraspinatus tendon from its origin in the supraspinatus muscle down to the area of attachment on the humerus. As is well understood in the art, loading of the tendon is in this general direction upon contraction of the supraspinatus muscle While some previous implants may encourage rapid tissue ingrowth (e.g., blood vessels and fibroblasts), the previous implants may not provide any additional strength to the damaged tendon until new tissue is induced. In some instances, it may be desirable to provide a tendon repair implant 25 which provides immediate mechanical strength to the tendon and also induces a healing response. This may be accomplished with a layered or composited implant 25. The implant 25 may include a first layer or component 50 having a first set of properties and a second layer or component 52 having a second set of properties. In some instances, the first layer 50 may be a bioinductive implant or component and the second layer 52 may be a higher-strength component. In some instances, the bioinductive component 50 and the higher-strength component 52 may be formed as a laminated structure. For example, the bioinductive component 50 and the higher-strength component 52 may be formed as discrete layers, as shown in FIG. 6A. In other instances, the implant 25 may include a transition region 51 between the layers 50, 52, such that the bioinductive component 50 and higher strength component 52 are blended in the transition region as shown in FIG. 6B. In yet other embodiments, the bioinductive component 50 and the higher-strength component 52 may be an integrated composite. For example, the higher-strength component 52 may be dispersed throughout the bioinductive component 50. The bioinductive component 50 and the higher-strength component 52 may have a different tensile modulus and a different tensile strength from one another. For example, the bioinductive component 50 may have properties which encourage tissue ingrowth, or a healing response, while the higher-strength component 52 may have properties which provide immediate mechanical strength, as will be discussed in more detail below.

The bioinductive component 50 may include a selected porosity and longitudinal pathways to encourage tissue in-growth. In some useful embodiments, the sheet-like structure of the bioinductive component 50 comprises a material defining a plurality of pores that encourage tissue growth therein. The porosity and tissue in-growth allows for new collagen to integrate with collagen of the native tendon for functional load carrying. A coating that encourages tissue growth or in-growth may be applied to the surfaces of the bioinductive component 50. It will be appreciated that sheet-like structure may comprise various pore defining structures without deviating from the spirit and scope of the present description. In some embodiments, the sheet-like structure has a pore size in the range of about 20 to about 400 microns. In some embodiments the pore size is in the range of about 100 microns to about 300 microns, and in some embodiments it is about 150 to about 200 microns. The porosity may be about 30% to about 90%, or it may be within the range of at least about 50% to about 80%. In some instances, the bioinductive component may have a dry density in the range of 0.2 grams per cubic centimeter ($g/cm^3$) to 0.4 $g/cm^3$. Examples of pore defining structures are discussed in more detail below for specific embodiments, but may include, but not be limited to open cell foam structures, mesh structures, micromachined layered structures and structures comprising a plurality of fibers. In some embodiments, the fibers may be interlinked with one another. Various processes may be used to interlink the fibers with one another. Examples of processes that may be suitable in some applications include weaving, knitting, and braiding.

The porosity of the bioinductive component 50 may be further structured to include tissue in-growth pathways in the longitudinal direction of the implant. Pathways may be included to extend through the thickness of the implant or laterally in the plane of the bioinductive component 50. Pathways may include segments extending longitudinally in the plane of the bioinductive component 50. In some embodiments, longitudinally extending pathways comprise a majority of the porosity with such pathway segments having cross sections of about 150 to about 200 microns. Longitudinal pathways may be open channels or lumens that extend in the longitudinal direction in the plane of the sheet-like structure when laying flat. They may be defined in the thickness of the sheet in the longitudinal direction. Further, these longitudinal pathways may generally be maintained when the implant 25 is subjected to longitudinal loads experienced during rehabilitation. However, large (3-5 centimeters) and massive (>5 centimeters) tears may involve more than one tendon. The collagen fibers in the different tendons will be oriented in different directions. Therefore, uniform orientation of the pathways and/or fibers of the implant 25 is not necessarily needed. It is contemplated that at least some of the pathways and/or fibers may be oriented in the lateral direction or at varying angles between the longitudinal and lateral directions.

It is contemplated that the initial tensile modulus of the bioinductive component 50 may be less than the tensile modulus of the supraspinatus tendon which is in the range of 50 MPa to 150 MPa. For example, the bioinductive component 50 may be designed to have a tensile modulus in the range of 5 MPa to 50 MPa. In some embodiments, the tensile modulus may be approximately 10 MPa.

It is desirable in some situations to generate as much tissue as possible within anatomical constraints. In some cases where a tendon is degenerated or partially torn, tendon loads are relatively low during early weeks of rehabilitation. For example, the load may be about 100 N. The strain in the tendon due to the load during rehabilitation can be about 2%. In some of these cases, the bioinductive component 50 can be designed to have an initial ultimate tensile strength of at least about 2 MPa. The tensile strength may be designed to be no more than about 50 MPa and no less than about 5 MPa with a failure load of approximately 50 N to 100 N. The compressive modulus may be designed to be at least about 0.2 MPa. Similarly, the suture pull-out strength may be relatively low. For example, the suture pull-out strength may be in the range of 5 N to 15 N.

In some embodiments, the bioinductive component 50 comprises one or more bioabsorbable materials. Examples of bioabsorbable materials that may be suitable in some applications include those in the following list, which is not exhaustive: polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly (amino acids), poly(alphahydroxy acid) or related copolymers materials. In some embodiments, the hydrothermal transition temperature may be selected to provide a desired absorption time. For example, a hydrothermal transition temperature of approximately 60° Celsius (° C.) may provide an absorption time in the range of 3 to 6 months.

The bioinductive component 50 may be configured to allow loading and retention of biologic growth factors. The bioinductive component 50 and/or the growth factors may be configured to controllably release the growth factors. The bioinductive component 50 may be configured to allow transmission of body fluid to remove any degradation byproducts in conjunction with a potential elution profile of biologics. The bioinductive component 50 may also include platelet rich plasma at the time of implant or other biologic factor to promote healing and tissue formation.

Figure 7:
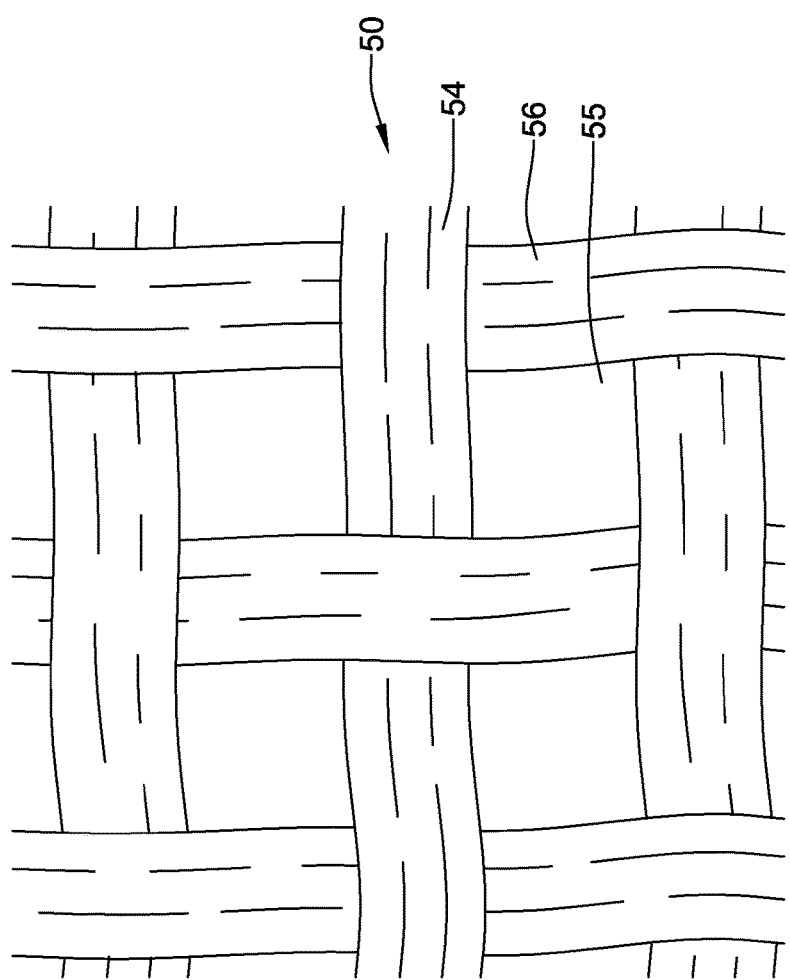
FIG. 7 is a schematic image of a portion of an exemplary tendon repair implant including a sheet-like structure having a woven strand and multifilament configuration.

One material and format for the sheet-like structure of the bioinductive component 50 is shown in FIG. 7. The structure 50 is a woven material including multiple strands 54 of a polymeric material, with each strand 54 including multiple filaments 56. The strands 54 include a weave pattern that forms longitudinally extending pathways 55. These longitudinally extending pathways 55 have a cross section of about 150 to about 200 microns as indicated. One material for the filaments is poly-L-lactic acid. Other illustrative materials and formats for the sheet-like structure of the bioinductive component 50 are found in commonly assigned U.S. Patent Publication Number 2011/0224702, which is herein incorporated by reference.

The second, or higher-strength, component 52 may be generally stronger than the first component 50, having both a higher initial tensile strength and a higher initial tensile modulus than the first component 50. For example, the second component 52 may have a tensile strength approximately equal to the tensile strength of the supraspinatus tendon, which may be in the range of 20 MPa to 30 MPa. The tensile strength of the second component 52 may be four to five times greater than the tensile strength of the bioinductive component. The second component 52 may have a failure load in the range of 200 N to 300 N.

To accomplish the desired degree of load sharing, the initial tensile modulus of the second component 52 should be in the same general range as the tensile modulus of the tendon. For example, the second component 52 may have a tensile modulus in the range of 50 MPa to 150 MPa. This may allow the initial load on the implant 25 to be in the range of 50% or more. It is contemplated that the implant 25 may need to carry loads in the range of 20 N to 80 N during rehabilitation.

The suture pull-out strength of the second component 52 may be higher than the suture pull-out strength of the first component 50. For example, the suture pull-out strength of all of the sutures combined needs to be sufficient to support the load of a worst case scenario (e.g. attachment of the implant to both bone and tendon). As noted above, the implant 25 may need to carry loads of up to 80 N. If four sutures are used to affix the implant 25, each suture would need a pull out strength in the range of about 20 N. It is contemplated that the suture pull-out strength may be increase by bonding or "welding" the first and second components 50, 52 together around the perimeter thereof.

The second component 52 may be designed to provide stress protection until the repaired tendon reattaches to the humeral head. This may occur over a time period of 3 to 6 months. Thus, the second component 52 may maintain its strength for at least 3 to 6 months, and in some instances, longer and then begins to biodegrade. The second component 52 may comprise one or more bioabsorbable materials. Examples of bioabsorbable materials that may be suitable in some applications include those in the following list, which is not exhaustive: polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly (hydroxybutyrate), polyanhydride, polyphosphoester; poly (amino acids), poly(alphahydroxy acid) or related copolymers materials. In some embodiments, the hydrothermal transition temperature may be selected to provide a desired absorption time. It is contemplated that the second component 52 may be absorbed more slowly than the bioinductive component 50. For example, the second component 52 may be completely absorbed in about one year. This is just an example. In some instances, the second component 52 may be formed of a material that is not bioabsorbable. The material of the second component 52 selected should be highly pure and have excellent biocompatibility in order to avoid and adverse inflammatory response.

Figure 8:
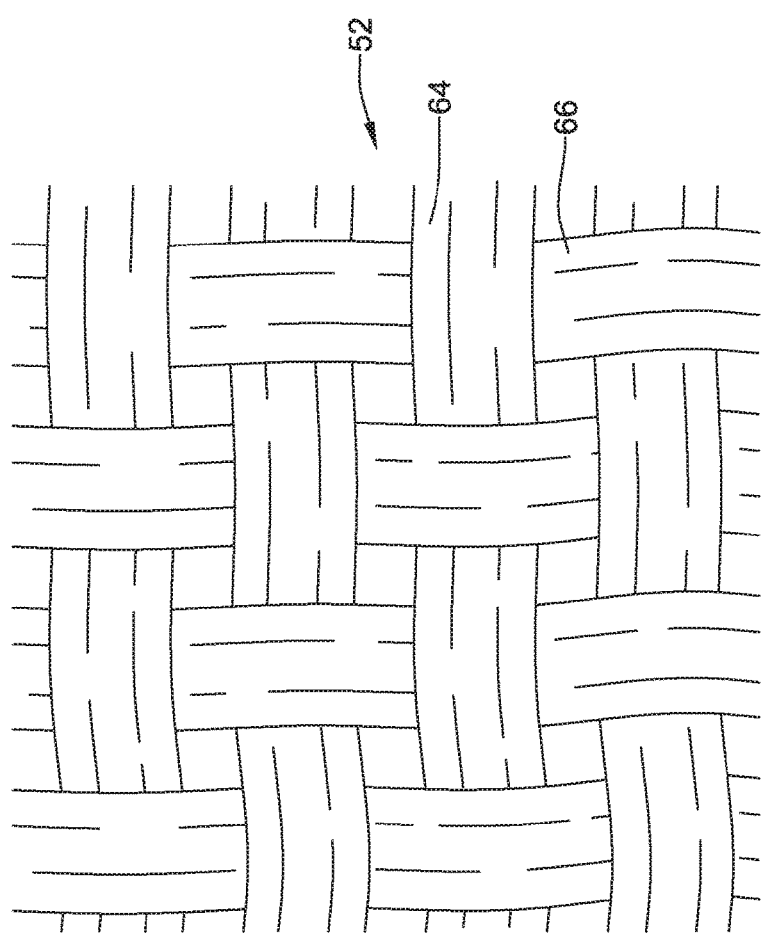
FIG. 8 is a schematic image of another portion of an exemplary tendon repair implant including a sheet-like structure having a woven strand and multifilament configuration
Figure 9:
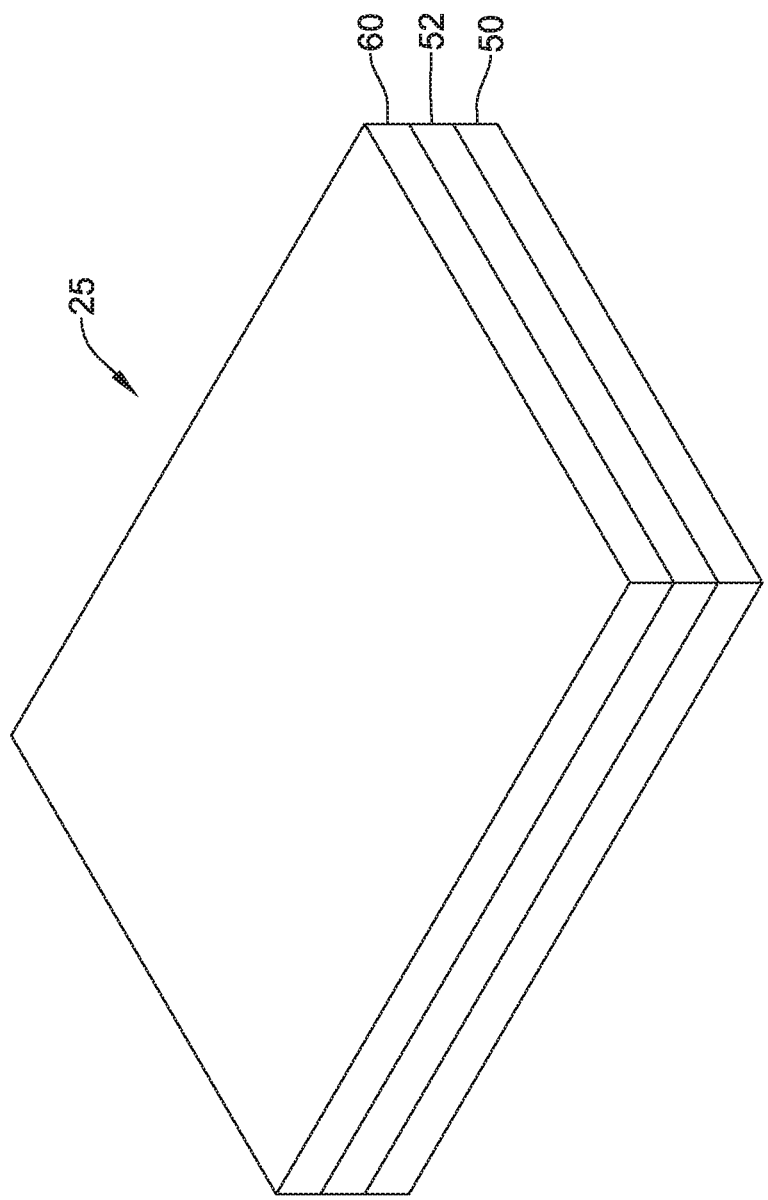
FIG. 9 is another schematic perspective view of the illustrative tendon repair implant of FIG. 6A.

One material and format for the sheet-like structure of the second component 52 is shown in FIG. 8. Similar to the structure shown in FIG. 7, the second component 52 may have a generally woven structure including multiple strands of a polymeric material 64. Each strand may include multiple filaments 66. The strands 64 may be generally woven. However, in some embodiments, the strands forming the second component 52 may be less oriented (more disordered) than the strands of the first component 50. For example, the fibers of the second component 52 may have a lattice type structure. This may increase the suture pull out strength of the second component 52.

In some embodiments, the second, high-strength, component 52 may include a decellularized dermal graft. Suitable decellularized dermal grafts may include a Conexa™ xenograft manufactured by Tornier, Inc. or Graftjacket® allograft manufactured by Wright Medical, Inc. It is contemplated that if a decelluarlized dermal graft is used as the second component 52, mechanical conditioning may be required to remove slack in the material. Due to this initial slack, current dermal grafts undergo about 20% to 30% elongation before they carry any significant load. For the purposes of the present invention, dermal grafts would need to be pre-stretched to remove the slack and delivered to the surgical site without reverting to the pre-stretched condition. Further processing may also be required in order to improve the purity of the material. The material should be highly pure and have excellent biocompatibility in order to avoid an adverse inflammatory response. The decellularized dermal graft could also be processed to incorporate fenestrations in order to create channels for tissue ingrowth.

In other embodiments, the second high-strength component 52 may include a synthetic implant. A suitable synthetic implant may include a woven mesh of poly-L-lactic acid, such as the X-Repair product manufactured by Synthasome. It is contemplated that if a synthetic implant is used as the second component 52, mechanical conditioning may be required to remove slack in the material, as described above for dermal grafts.

It is contemplated that the second component 52 may be formed of the same material as the first component 50. However, the mechanical properties of the second component 52 may be different from those of the first component 50. For example, the second component 52 may be made denser, less porous, and/or have increased cross-linking relative to the first component 50 to provide a material having increased strength, as detailed above. However, in some embodiments, the first component 50 and the second component 52 may be formed from different materials.

As discussed above, the implant 25 may be formed from a layer of a first bioinductive component 50 and a second higher strength component 52. In some instances, the higher strength component 52 may be layered on top of the bioinductive component 50. When the implant 25 is positioned within the body, the bioinductive component 50 is placed into contact with the tendon to encourage tissue in-growth. In some embodiments, the second component 52 may be a high strength modification of the first component 50. For example, the second component 52 may be formed of the same material as the first component 50, but have a higher density, lower porosity, and/or an increased degree of cross-linking relative to the first component 50. As discussed above, the implant 25 may have a thickness T in the range of 1 mm to 3 mm when dehydrated. In some embodiments, the first component 50 and the second component 52 may have the same thickness. For example, the first component 50 may have a thickness of 1 mm and the second component 52 may also have a thickness of 1 mm. In other embodiments, the second component 52 may have a greater thickness than the first component 50, or vice versa. Increasing the thickness of the second, higher strength component 52 may increase the tensile strength of the implant 25.

Figure 10:
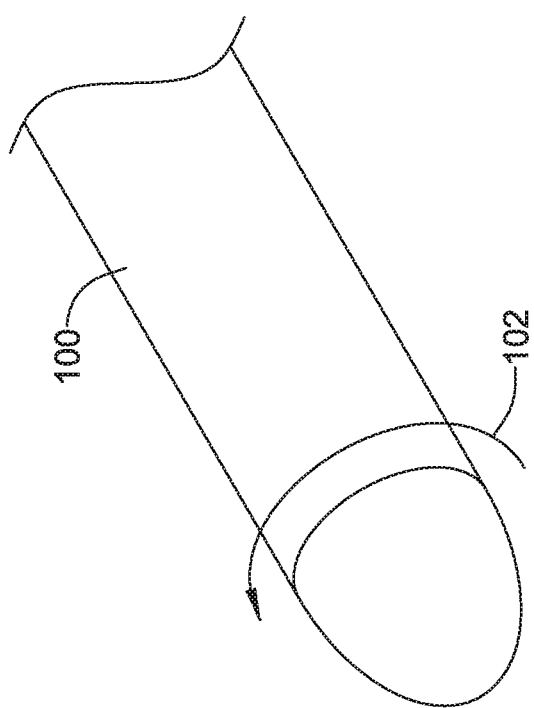
FIG. 10 is a schematic of a mandrel used to manufacture an illustrative tendon repair implant.

In some embodiment's, the implant 25 may be formed by collecting fibers, such as, but not limited to, collagen fibers, on a rotating mandrel 100, as shown in FIG. 10. The first component 50 may be formed by rotating 102 the mandrel 100 at a first speed. Once the desired thickness of the first component 50 has been obtained, the mandrel 100 may be rotated 102 at a second speed, slower than the first speed. The mandrel 100 continues to collect the fibers at the second, slower speed. However, the decreased speed of rotation will result in less orientation of the fibers and a denser packing of the fibers to form the second, higher strength component 52. The continuity of the fiber collection process provides continuity between the first component 50 and the second component 52, effectively affixing the two components 50, 52 to one another to form the layered implant 25. The thickness of each component 50, 52 can be adjusted as necessary to achieve the desired final properties by adjusting the length of time fibers are collected at each rotation speed. It is contemplated that the process may be reversed and the second component formed first. In some instances, variation of the fiber collection process during build-up of the implant 25 may be used to produce a "fiber-reinforced" bioinductive component 50 in which the high-strength component 52 is distributed throughout the low-strength component 50, without distinct separate "layers". For example, on a semi-continuous basis such as not to form distinct layers, collection of fibers with more orientation could be alternated with collection of fibers with less orientation in order to produce a "self-reinforced" composite structure. In some embodiments synthetic fibers, such as, but not limited to absorbable suture material, may be incorporated into the bioinductive component 50 during the manufacturing process to create a reinforced composite material which is capable of invoking a healing response as well as providing immediate strength to the tendon.

In other embodiments, the first component 50 and the second component 52 may be formed as separate layers. The layers 50, 52 may then be stacked one on top of the other and freeze-dried or lyophilized to form a composite. The composite is then cross-linked to form a link or bond between the first component 50 and the second component 52. The link or bond between the first component 50 and the second component 52 does not need to be a high-strength interface. The bond only needs to be sufficient enough to hold the two components 50, 52 together to enable handling during surgery. As such, freeze-drying wet components 50, 52 after they have been stacked one on top of the other may sufficiently bond (at least temporarily) the two components to enable the implant 25 to be surgically implanted. Alternatively, the two components 50, 52 may be stitched together using, for example, bioabsorbable suture material. It is contemplated that stitching the components 50, 52 may be used in combination with or in place of the freeze-drying and/or cross-linking.

It is contemplated that if the high-strength component 52 is formed of the same material as the bioinductive component 50 and is made stronger by increased cross-linking, the components 50, 52 may need to be produced and cross-linked separately. The two components 50, 52 may then be laminated or bonded as described above.

FIG. 8 is a perspective, schematic view of the illustrative tendon repair implant 25 including a third component, or layer 60. In some embodiments, the third component 60 may be an additional low-strength, or bioinductive, component positioned on top of the second, high-strength component 52 to create an implant 25 including three layers. It is contemplated that the bioinductive component 60 may be affixed or secured to the high-strength component using any of the methods described above.

According to aspects of the present detailed disclosure, methods of treating a complete or partial thickness tear in a tendon are also provided. In some methods, supraspinatus tendons having complete tears, partial thickness tears of greater than 50% and/or partial thickness tears of less than 50% are treated. The treatment site may be first arthroscopically accessed in the area of the damaged tendon. A tendon repair implant, such as previously described may be placed over a partial tear in a tendon. In some embodiments, the implant may be placed over a tendon having complete or partial tear(s), abrasions and/or inflammation. Left untreated, minor or partial tendon tears may progress into larger or full tears. According to aspects of the present disclosure, a complete or partial tear may be treated by protecting it with a tendon repair implant as described above. Such treatment can promote healing and provided immediate strength to the tendon, as well as prevent more extensive damage from occurring to the tendon, thereby averting the need for a more involved surgical procedure.

For arthroscopic delivery of the tendon repair implant, the implant may be configured to be collapsible so that it may be inserted into or mounted on a tubular member for arthroscopic insertion to the treatment site. For example, the implant and associated delivery device may be collapsed like an umbrella where the deployed delivery systems unfolds the pleats of the implant as mounted thereon to allow surface to surface engagement with the tendon without any substantial wrinkles. Once flat against the tendon, the tendon repair implant may then be affixed using sutures or other suitable means such as staples such that the tensile properties will assure that the anatomical load will be shared because the native tendon and implant experience the same strain under load.

In summary, the tendon repair implant may comprise an absorbable material. In some embodiments, the purpose of the implant is to protect an injured portion of a tendon during healing, provide an implant for new tissue growth, and/or temporarily share some of the tendon loads. The implant may induce additional tendon-like tissue formation, thereby adding strength and reducing pain, micro strains and inflammation. When implanted, the implant 25 may provide immediate strength to the tendon and transfer the load to the native tendon as the tendon heals and the implant 25 biodegrades. In some embodiments, organized collagen fibers are created that remodel to tendon-like tissue or neo-tendon with cell vitality and vascularity. Initial stiffness of the device may be less than that of the native tendon so as to not overload the fixation while tendon tissue is being generated.

Material(s) used in the implanted device should be able to withstand the compression and shear loads consistent with accepted post surgical shoulder motions. The perimeter of the device may have different mechanical properties than the interior of the device, such as for facilitating better retention of sutures, staples or other fastening mechanisms. The material(s) may be chosen to be compatible with visual, radiographic, magnetic, ultrasonic, or other common imaging techniques. The material(s) may be capable of absorbing and retaining growth factors with the possibility of hydrophilic coatings to promote retention of additives.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed:

1. A tendon repair implant comprising:
a sheet-like structure including a first component configured to have an initial tensile modulus of about 5 megapascals (MPa) to 50 MPa and comprising a plurality of pores for tissue in-growth and a second component configured to have an initial tensile modulus of about 50 MPa to 150 MPa, wherein the initial tensile modulus of the second component is different from the initial tensile modulus of the first component;
wherein the sheet-like structure conforms to the surface of the tendon and is configured to have an initial load share representing about 50% or more of the load of the tendon when affixed to the tendon.

2. The tendon repair implant of claim 1, wherein the first component and the second component form discrete layers.

3. The tendon repair implant of claim 1, wherein the second component is intermixed with the first component to form a composite material.

4. The tendon repair implant of claim 1, wherein about 50% or more of the load of the tendon comprises between 25 Newtons (N) and 50 N.

5. The tendon repair implant of claim 1, wherein the sheet-like structure is configured to degrade in tensile strength from an initial tensile strength thereby sharing less of the load of the tendon over time but retain at least about 50% of the initial load share of the sheet-like implant three months after being affixed to the tendon.

6. The tendon repair implant of claim 1, wherein the first component is configured to degrade in tensile strength from an initial tensile strength at a first rate and the second component is configured to degrade in tensile strength from an initial tensile strength at a second rate different from the first rate.

7. The tendon repair implant of claim 6, wherein the second rate is slower than the first rate.

8. The tendon repair implant of claim 1, wherein the first component comprises a bioresorbable material.

9. The tendon repair implant of claim 1, wherein the second component comprises a bioresorbable material.

10. The tendon repair implant of claim 1, wherein the first component comprises a polymer material.

11. The tendon repair implant of claim 1, wherein the second component comprises a polymer material.

12. The tendon repair implant of claim 1, wherein the sheet-like structure is further configured to be attached to the surface of the tendon without significant pre-loading or significant pre-stretching.

13. The tendon repair implant of claim 1, wherein the sheet-like structure has one or more coatings affixed thereto which promote tissue in-growth.

14. The tendon repair implant of claim 1, wherein the pores have sizes between about 20 microns and 400 microns.

15. The tendon repair implant of claim 1, wherein the sheet-like structure is defined by a longitudinal dimension, a lateral dimension, and a thickness dimension, wherein the longitudinal dimension is greater than the lateral dimension and the thickness dimension, and wherein the sheet-like structure further comprises one or more longitudinal pathways extending along the longitudinal dimension of the sheet-like structure.

16. The tendon repair implant of claim 1, wherein the sheet-like structure has a maximum of about 0.5% creep over three months.

17. The tendon repair implant of claim 1, further comprising a third component configured to have an initial tensile modulus of about 5 MPa to 50 MPa.

18. A tendon repair implant for repair of a complete or partial thickness tear of a supraspinatus tendon having a load bearing direction, the tendon repair implant comprising:
- a sheet-like structure having a longitudinal dimension, a lateral dimension, and a thickness dimension and configured to be affixed to a surface of the supraspinatus tendon such that the longitudinal dimension of the sheet-like structure extends generally parallel to the load bearing direction of the supraspinatus tendon, the sheet-like structure including:
  - a first component configured to have an initial tensile modulus of about 5 megapascals (MPa) to 50 MPa, the first component comprising a plurality of pores for tissue in-growth and that include a plurality of longitudinal pathways that encourage tissue in-growth therein, wherein the longitudinal pathways extend along the longitudinal dimension of the sheet-like structure and have cross sections of about 150 microns to 200 microns; and
  - a second component configured to have an initial tensile modulus of about 50 MPa to 150 MPa, the second component having a porosity less than a porosity of the first component;
- wherein when affixed to the surface of the supraspinatus tendon, the sheet-like structure is configured to initially share about 50% or more of a load applied to the supraspinatus tendon.

19. The tendon repair implant of claim 18, wherein the first component and the second component form discrete layers.

20. The tendon repair implant of claim 18, wherein the second component is intermixed with the first component to form a composite material.

21. The tendon repair implant of claim 18, wherein the pores range in size from about 20 to 400 microns.

* * * * *